US006962585B2

(12) United States Patent
Poleo, Jr.

(10) Patent No.: US 6,962,585 B2
(45) Date of Patent: Nov. 8, 2005

(54) CATHERIZATION SYSTEM AND METHOD (76) Inventor: Louis A. Poleo, Jr., 6001 Figland St., Pearland, TX (US) 77450

( * ) Notice: Subject to any disclaimer, the term of this patent is extended or adjusted under 35 U.S.C. 154(b) by 8 days.

(21) Appl. No.: 10/302,076

(22) Filed: Nov. 22, 2002

(65) Prior Publication Data

US 2004/0102766 A1    May 27, 2004

(51) Int. Cl.[7] .............................................. A61B 18/18
(52) U.S. Cl. .......................................... 606/7; 606/15
(58) Field of Search .......................... 606/7, 8, 14–16, 606/27, 28

(56) References Cited

U.S. PATENT DOCUMENTS

| 4,175,538 A |   | 11/1979 | McCarty |   |
|---|---|---|---|---|
| 4,672,961 A | * | 6/1987 | Davies | 606/7 |
| 4,735,201 A | * | 4/1988 | O'Reilly | 606/28 |
| 4,913,142 A | * | 4/1990 | Kittrell et al. | 606/7 |
| 4,994,060 A | * | 2/1991 | Rink et al. | 606/28 |
| 5,193,526 A | * | 3/1993 | Daikuzono | 606/15 |

OTHER PUBLICATIONS

"Dorland's Pocket Medical Dictionary", Copyright 1989, 24th Edition, p. 276 & 476, W. B. Saunders Company, Philadelphia, Pennsylvania, U.S.
St. J. Taylor, et. al., "Design Aspects and Operation Characteristics of the Lightweight Chemical Detector" IJIMS, 1(1998)1, pp. 58-63, Copyright 1998, International Society for Ion Mobility Spectrometry, U.S.
Dennis R. Trumble, et. al., "Copulsation Balloon for Right Ventricular Assistance"Copyright 1999, pp. 1-8, Circulation 1999; 99:2815-2818, American Heart Association; U.S.
"Medical Product Selector Guide, Adhesives For Medical Device Assembly", Copyright 2000, 6 pages unnumbered, Loctite Corporation, U.S.
"Webster's College Dictionary", Copyright 1995, pp. 1040, 1208-1209, Random House, Inc., U.S.
"Webster's II New Riverside University Dictionary" Copyright 1988, pp. 578,906,&1052, Houghton Mifflin Company, U.S. , Publisher: The Riverside Publishing Co.

* cited by examiner

*Primary Examiner*—Michael Peffley
(74) *Attorney, Agent, or Firm*—Gerald E. Lester (57) ABSTRACT

An artery blockage removal system including a hollow plastic tube with IR optical fibers extending longitudinally between its inner and outer walls, the end of the tube having a metal clad tip ring preferably of gold abutting against the end of the IR optical fibers, and the outer surface of the hollow plastic tube having curved arterial guards molded into its outer circumference to hold the inner walls of the artery away from the hollow plastic tube and metal clad tip ring to avoid physical and thermal damage to the inner artery walls, whereby arterial blockage is removed through application of the metal clad tip ring heated by the IR optical fibers and a vacuum applied through the center of the hollow tubing.

18 Claims, 6 Drawing Sheets

CATHERIZATION SYSTEM AND METHOD

FIELD OF THE INVENTION

The invention is related generally to catherization systems, and more particularly to an IR optical fiber catherization system for dislodging arterial blockage and removing resulting arterial debris through application of a vacuum without any damage occurring to artery walls.

BACKGROUND OF THE INVENTION

Systems for removing arterial debris are known which vary from use of lasers, heated coils, or stents for vaporizing arterial blockage, to mechanical devices such as vibrating conical sandpaper for abrading, so-called nibbler chomping pistons for biting, or rotating blades for cutting the blockage away from the artery walls.

An Excimer Laser Coronary Angioplasty system and procedure offered by Spectranetics of Colorado Springs, Colo., involves the insertion into an artery of a laser catheter containing a bundle of optical fibers and a stent with a guide wire. The laser catheter is advanced in the artery until the guide wire crosses a blockage, at which time bursts of ultraviolet (cool) laser light is transmitted through the fiber optic fibers to open a hole in the blockage. Thereafter, an x-ray contrast dye is injected into the blood stream to determine the extent to which the artery has been opened. This procedure does not remove substantial amounts of blockage because ultra violet radiation is too cool to melt the blockage. Rather, a hole is blasted through the blockage to accommodate the admission of a stent. While the catherization system includes a filter, the filter is not sufficient to catch all debris which may flow downstream.

Such prior systems have failed because they have not effectively removed arterial blockage from the artery walls, and have not effectively removed arterial debris from the artery once the arterial blockage has been dislodged. In addition, such prior systems have not adequately protected the artery walls from physical or thermal injury. Further, many of the prior art devices embody numerous parts which tend to fail or shatter in a high temperature/high vacuum environment.

In the catherization system of the present invention, infrared radiation is used to vaporize arterial blockage and remove it from the artery walls, and arterial guards are used to protect the artery walls from physical and thermal injury. Further, a vacuum chamber is formed within the inner walls of a hollow cylindrical tube comprising the catherization system to remove all arterial debris before it can flow into the body blood stream.

SUMMARY OF THE INVENTION

The present invention is directed to an IR (infrared) optical fiber catherization system and method for dislodging blockage from artery walls without injury to the artery. The catherization system includes a central vacuum passageway for removing the resulting arterial debris from the artery to prevent injury caused by such debris entering the main blood stream of the body. The catherization process includes the following steps: X-Ray dye is injected into an artery to pinpoint the location of a blockage; a guidewire of the catherization system is inserted into the artery to cross the location of the blockage; the catherization system is advanced along the guide wire to abut the blockage; IR and vacuum sources are activated respectively to dislodge the blockage from the artery walls and remove arterial debris without damage to the artery and without risk of debris entering the body blood stream.

In one aspect of the invention, the catherization system of the present invention is comprised of a hollow cylindrical tube having a metal clad tip ring at one end, with the circumference of the ring most distant from the end of the tube being larger than the circumference of the ring abutting the end of the tube.

In a further aspect of the invention, arterial guards are molded into the outer surface of the hollow cylindrical tube and have curved flanges extending outward in parallel to the latitudinal axis of the tube to abut the artery walls without injury to the artery. The arterial guards hold the artery walls away from the metal clad tip ring to avoid heat injury to the inner artery walls, and create blood stream flow paths in addition to the central vacuum passageway of the hollow tubing.

In another aspect of the invention, IR optical fibers extend along the longitudinal axis between the inner and outer walls of the hollow cylindrical tube and abut the lower surface of the metal clad tip ring to heat the ring sufficiently to vaporize arterial blockage.

In still another aspect of the invention, the metal clad tip ring is preferably of gold for efficient heat transfer, and the outer surface of the hollow cylindrical tube is coated with Teflon to further avoid thermal injury to the inner artery walls.

In a still further aspect of the invention, the ends of the IR optical fibers abutting the lower surface of the metal clad tip ring are positioned equidistant from the ring's center and are separated by equidistant arcs along a circular path between the inner and outer circumferences of the metal clad tip ring.

In yet another aspect of the invention, the hollow cylindrical tube and IR optical fibers are made of IR specific plastic to avoid splintering in a high temperature/high vacuum environment.

BRIEF DESCRIPTION OF THE DRAWINGS

Additional objects, features and advantages of the present invention will become apparent from the following detailed description when read in conjunction with the accompanying drawings in which.

DESCRIPTION OF PREFERRED EMBODIMENTS

Preferred embodiments of the invention will now be described with reference to the accompanying drawings.

The following definition, whether occurring with capitalizations or in lower case, is used consistently throughout this specification in disclosing the invention:

"Stent" shall mean a coil comprised of an alloy such as nickle-titantium or stainless steel, which works in conjunction with an internal angioplasty balloon to expand the stent to the walls of an artery.

Figure 1:
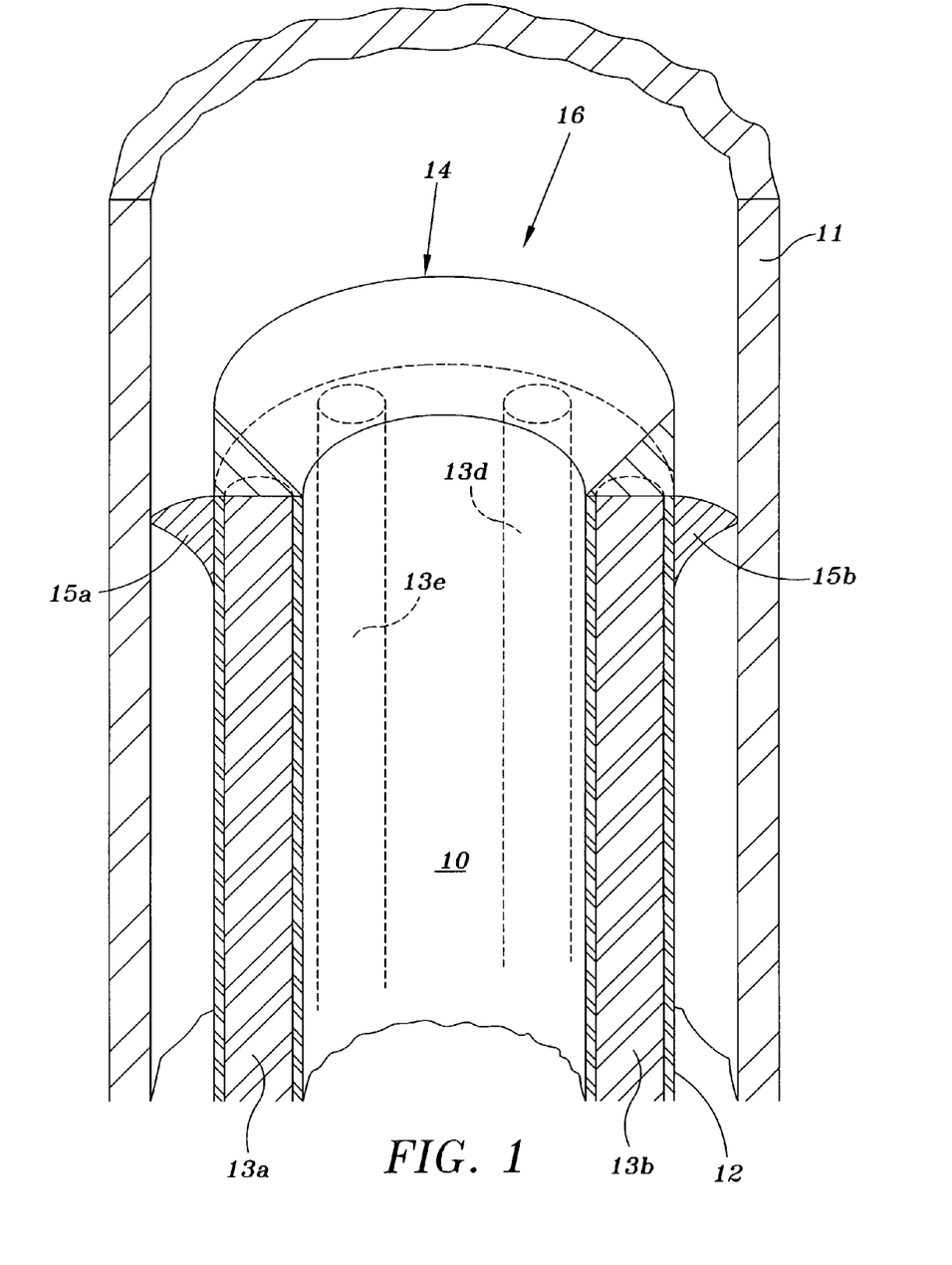
FIG. 1 is a cross-sectional view along 1—1 of FIG. 2 of a first embodiment of the present invention with arterial guards.

Referring to FIG. 1, a hollow cylindrical tube 10 having a wall thickness of the order of 0.25 millimeters, and an outer circumference of the order of 1.5 millimeters is shown inserted into an artery 11. An artery generally has an inner wall diameter of the order of 2.00 millimeters. A 0.25 micrometer Teflon coating 12 covers the outer surface of the hollow cylindrical tube 10. IR optical fibers 13a, 13b, 13d, and 13e are shown to be pneumatically sealed between the inner and outer walls of the hollow cylindrical tube 10, and extend the longitudinal length of the tube to abut the lower surface of a metal clad tip ring 14. Arterial guards 15a and 15b are molded into the outer surface of the hollow cylindrical tube 10 and act to separate the inner artery walls from the tube and the metal clad tip ring 14. In the embodiment of FIG. 1, the upper end of the arterial guards is aligned horizontally with the upper end of the hollow cylindrical tube 10.

The hollow cylindrical tube 10 with outer Teflon coating 12; IR optical fibers 13a, 13b, 13d, and 13e; metal clad tip ring 14, and arterial guards 15a and 15b comprise a first embodiment of the catherization system of the present invention.

The hollow cylindrical tube 10 with arterial guards 15a and 15b, and with pneumatically sealed IR optical fibers 13a, 13b, 13d, and 13e, may be commercially formed of a flexible polyvinal chloride (DEHP) type of plastic by any of numerous plastic product manufacturers such as PLAS-LABS of Lansing, Mich. The metal clad tip ring 14 is preferably gold, and may be manufactured commercially by any of numerous metallurgists including those generally used by hospitals.

In operation, dye is inserted into the artery 11 to pinpoint the exact location of artery blockage by X-ray. The catherization system generally referred to by reference number 16 thereafter is inserted into the artery 11, and the metal clad tip ring 14 is pushed against the artery blockage to be removed. A vacuum is then created within the inner walls of the hollow cylindrical tube 10, and an IR source is activated to irradiate the metal clad tip ring 14 by way of the optical fibers 13a, 13b, 13d, and 13e. The IR optical fibers are raised to a temperature in excess of 172 degrees Fahrenheit to heat the metal clad tip ring 14 and thereby thermally cut a passage through the artery blockage. The vacuum created in the hollow cylindrical tube 10 is in the range of 12 to 14 inches of mercury, and accommodates a blood current by which artery debris resulting from the above operation is removed through the longitudinal passageway created by the inner walls of the tube without allowing any debris to escape to the body blood stream. During the above process, the artery guards 15a and 15b allow blood to flow around the catherization system 16 to downstream tissues. Upon the artery debris being removed, the catherization system 16 is removed from the artery 11, which is restored to its normal functions.

Figure 2:
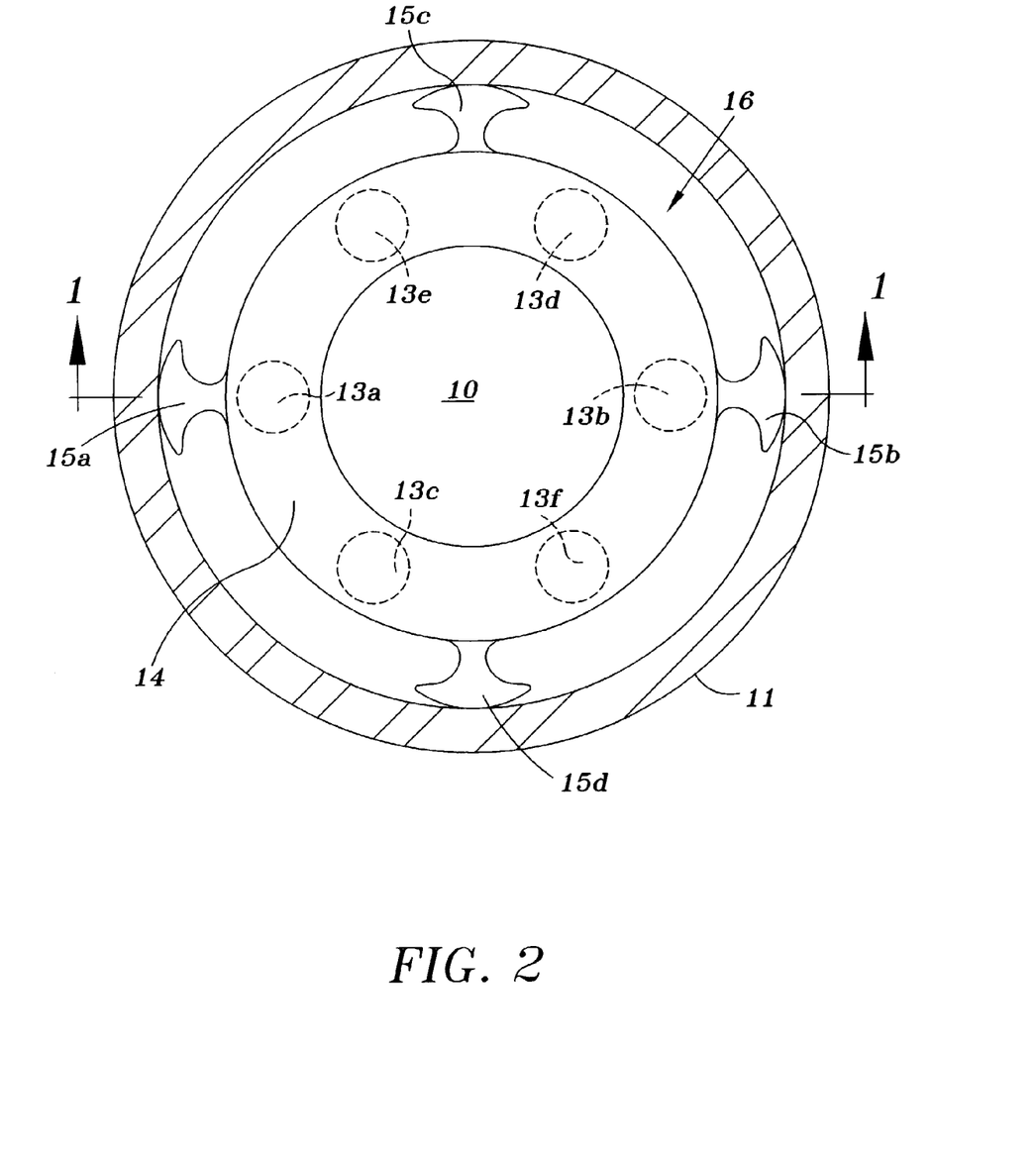
FIG. 2 is a cross-sectional view of the embodiment of the present invention illustrated in FIG. 1 along its latitudinal axis.

Referring to FIG. 2, a cross-section along the latitudinal axis of the embodiment of the invention illustrated in FIG. 1 is shown. The catherization system 16 is shown inserted into artery 11, with ends of IR optical fibers 13a–13f abutting the lower surface of the metal clad tip ring 14. The optical fibers 13a–13f are spaced apart by 60 degrees about a latitudinal circumference between the inner and outer walls of the hollow cylindrical tube 10. The inner wall of the artery 11 is spaced apart from the metal clad tip ring 14 by the arterial guards 15a–15d, which are separated by 90 degrees around the outer circumference of the hollow cylindrical tube 10. The arterial guards protect the inner walls of the artery from thermal as well as physical damage during a catherization process, and allow blood flow around the catherization system during a debris removal process.

In operation, the catherization system 16 is inserted into artery 11 with the IR optical fibers 13a–13f abutting the underside of the metal clad tip ring 14. As the catherization system 16 is moved against arterial blockage in the artery 11, the arterial guards 15a–15d having curved flanges hold the inner walls of the artery from contact with the hollow cylindrical tube 10 and metal clad tip ring 14, thereby avoiding physical and thermal damage to the artery. The artery is further protected by the Teflon coating 12 on the outer surface of the hollow cylindrical tube 10. When the metal clad tip ring 14 is heated by the IR optical fibers to a temperature of the order of 172° Fahrenheit, a passage is thermally cut through the arterial blockage without damaging the artery. As the artery blockage is dislodged, artery debris is created which is removed by means of a vacuum created in the longitudinal passageway formed by the inner walls of the hollow cylindrical tube 10. Upon the artery debris being removed, the catherization system 16 is removed from the artery 11, which resumes its normal functions.

Figure 3:
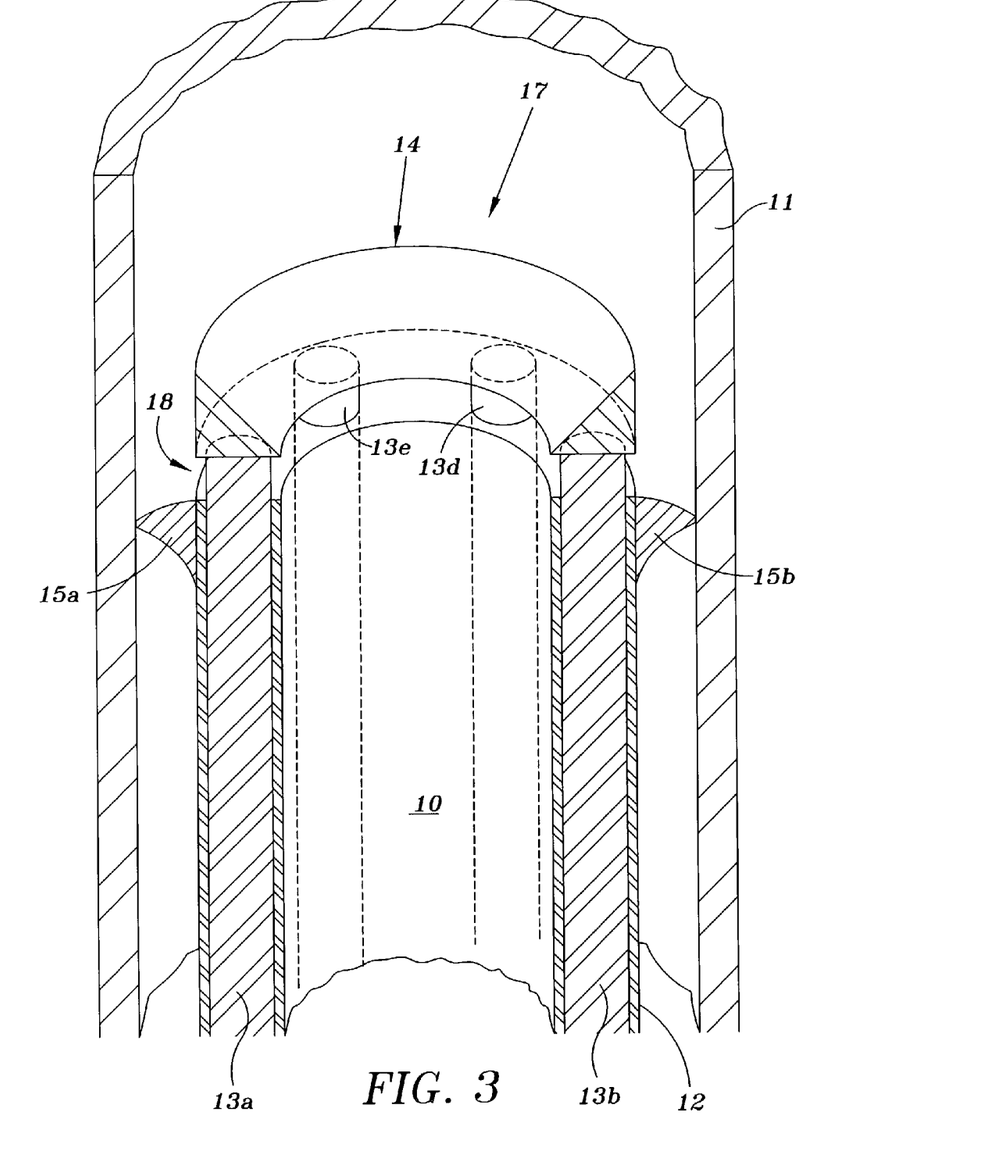
FIG. 3 is a cross-sectional view of a second embodiment of the present invention along its longitudinal axis that shows a longitudinal displacement between the metal clad tip ring 14 and the IR optical fibers 13a, 13b, 13d, and 13e to provide added flow paths into the interior of hollow cylindrical tube 10.

FIG. 3 illustrates an embodiment of the invention in which increased blood flow paths are created for a less restricted blood flow during the catherization process. The catherization system 17 of FIG. 3 differs from the catherization system 16 of FIG. 1 only by a longitudinal separation in the range of 1 to 2 millimeters being inserted between the underside of the metal clad tip ring 14 and the upper end of the hollow cylindrical tube 10. More particularly, the uppermost end of the optical fibers as represented by reference numbers 13a, 13b, 13d, and 13e are fabricated into the underside of the metal clad tip ring 14 to hold the metal clad tip ring separate from the hollow cylindrical tube 10. A further blood current path 18 is thereby created into the hollow cylindrical tube 10 for removal of the arterial debris by means of a vacuum being created within the hollow cylindrical tube 10 as before described.

Figure 4:
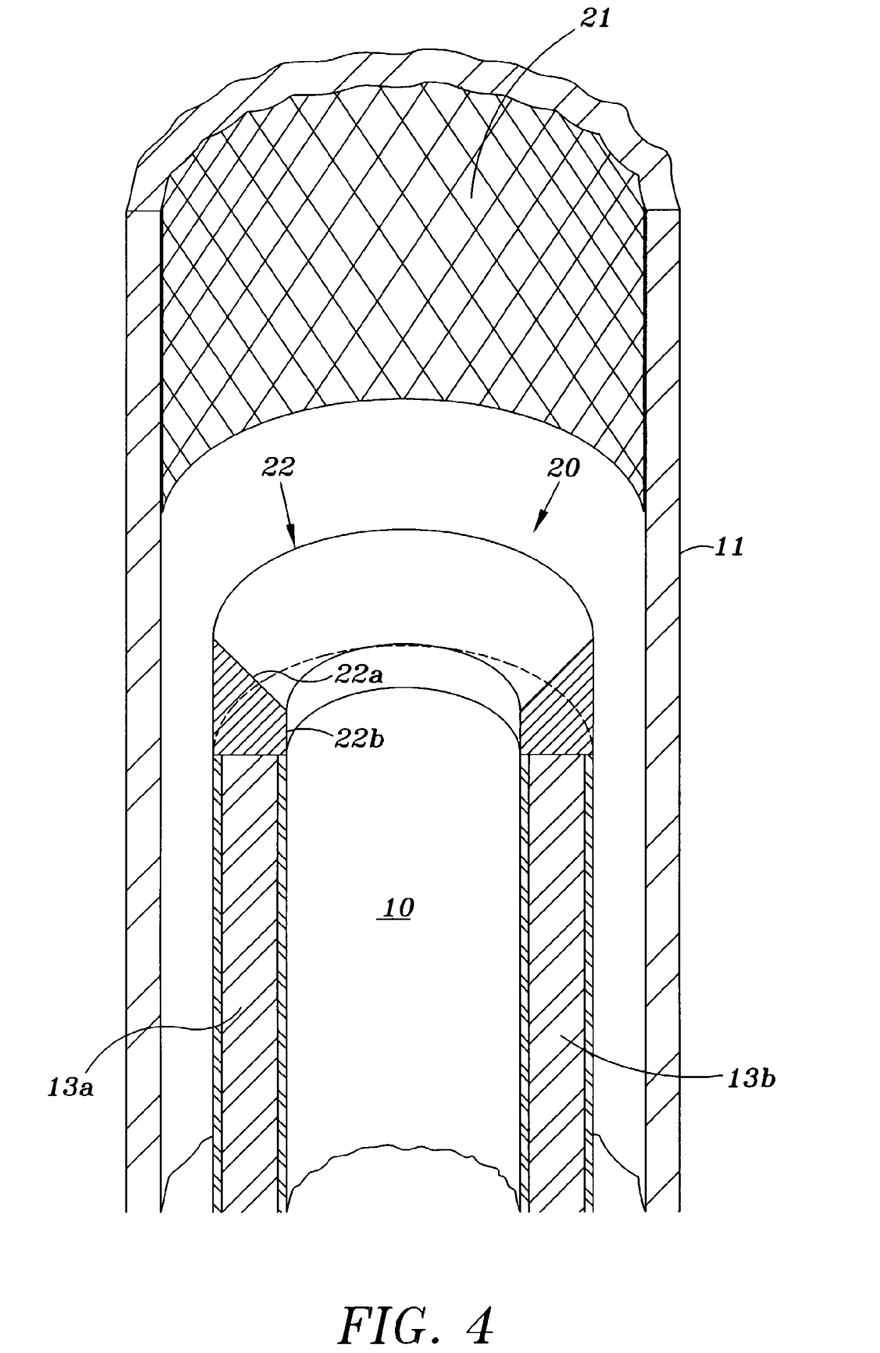
FIG. 4 is a cross-sectional view along the longitudinal axis of a third embodiment of the present invention which is used in combination with a stent.

FIG. 4 illustrates a third embodiment of the invention as used in conjunction with a stent. The catherization system 20 differs from the catherization system 16 of FIG. 1 only by the absence of arterial guards and Teflon coating 12, and the design of the metal clad tip ring 22. Referring to FIG. 4, a stent 21 is first inserted into the artery 11 to abut any arterial blockage previously found by use of an X-ray dye. IR optical fibers as represented by reference numbers 13a and 13b are shown to be pneumatically sealed between the inner and outer walls of the hollow cylindrical tube 10, and extend the longitudinal length of the tube to abut the lower surface of the metal clad tip ring 22. In operation, the stent 21 is pressed against the inner walls of the artery 11 through use of a water filled balloon internal to the stent. Thereafter, the catherization system 20 is advanced into the stent 21 to abut the artery blockage. A vacuum is then created within the inner walls of the hollow cylindrical tube 10, and an IR source is activated to irradiate the metal clad tip ring 22 by way of the optical fibers 13a and 13b. The IR optical fibers are raised to a temperature in excess of 172 degrees Fahrenheit to heat the metal clad tip ring 22 and thereby thermally cut a passage through the artery blockage. The increased surface areas 22a and 22b of the metal clad tip ring 22 ensure that the entry into the interior of the hollow cylindrical tube 10 does not become clogged by arterial debris. A vacuum in the range of 12 to 14 inches of mercury is created in the hollow cylindrical tube 10 to form a blood current by which artery debris resulting from the above operation is removed through the longitudinal passageway created by the inner walls of the hollow cylindrical tube 10. No arterial debris is allowed to escape to the body blood stream.

Figure 5:
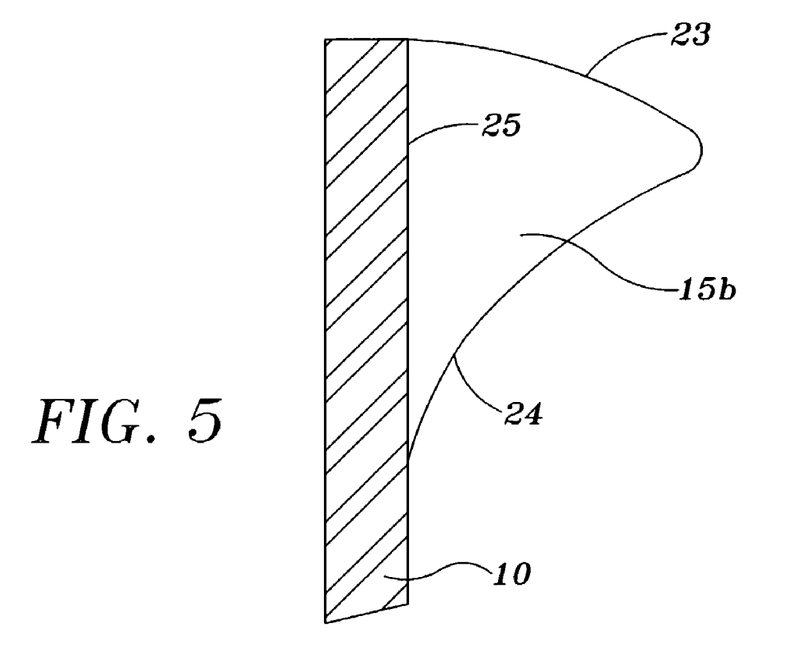
FIG. 5 is a side view of an arterial guard used in conjunction with the present invention as depicted in FIGS. 1–3 above.

Referring to FIG. 5, a side view of arterial guard 15b of FIG. 1 is shown. As before stated, the arterial guard 15b, which is representative of arterial guards 15a–15d, is formed to the outer surface of the hollow cylindrical tube 10. All edges of the arterial guard 15b are rounded to avoid any physical damage to the inner walls of the artery. Again referring to FIG. 5, an upper surface 23 of the arterial guard extends a horizontal distance of 0.25 millimeters from the outer surface of the hollow cylindrical tube 10. The upper surface 23 is formed as an arc of a circle having a radius of 0.50 millimeters. A surface 24 of arterial guard 15b is formed as an arc of a circle having a radius of 0.50 millimeters. A vertical distance 25 along the outer surface of the hollow cylindrical tube 10 and between upper surface 23 and surface 24 is 1.0 millimeters.

Figure 6:
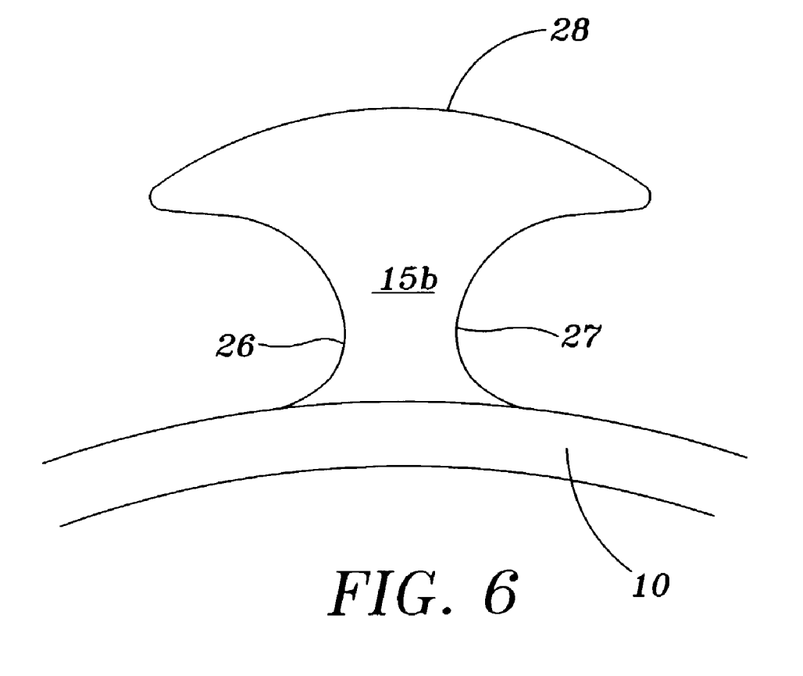
FIG. 6 is a top view of the arterial guard of FIG. 5.

Referring to FIG. 6, a top view of the arterial guard 15b is shown wherein an outer surface 28 at its furthest point is a distance of 0.25 millimeters from the outer surface of the hollow cylindrical tube 10. The outer surface 28 is formed as an arc of a circle having a radius of 0.50 millimeter. The surfaces 26 and 27 of the arterial guard 15b are formed as arcs of a circle having a radius of 0.625 millimeters.

Figure 7:
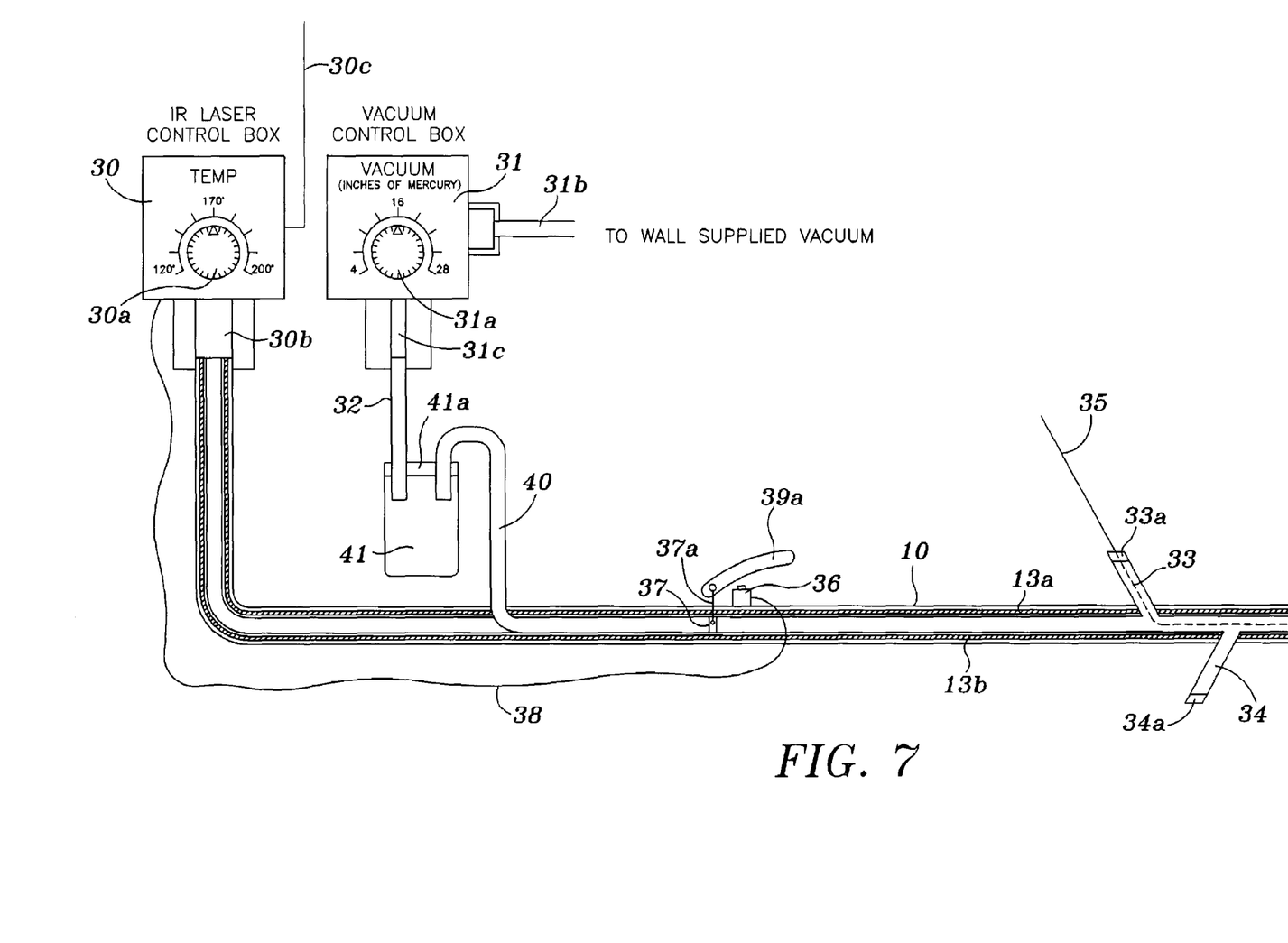
FIG. 7 is a functional block diagram of the electrical, IR, and vacuum source support system which is used with the embodiments of the invention illustrated in FIGS. 1–4 in an operating room environment.

FIG. 7 is a functional block diagram of a support system (which includes an IR source and a vacuum system) that services the metal clad tip ring 14 of FIGS. 1–3 and metal clad tip ring 22 of FIG. 4. More particularly, an IR laser control box 30 with control dial 30a and output node 30b applies infrared radiation to the IR optical fibers 13a and 13b which are sealed between the inner and outer walls of the hollow cylindrical tube 10, and which abut the underside of a metal clad tip ring as illustrated in FIGS. 1–4. Referring again to FIG. 7, the control box 30 is electrically connected by way of a conducting line 30c to a 110 volt AC source. Control box 30 may be any of numerous well known laser source products including those offered commercially by LUMENIS of Salt Lake City, Utah.

A vacuum control box 31 with control dial 31a is connected by way of a pneumatic connector 31b to a central vacuum source, and by way of a pneumatic connector 31c to a vacuum tube 32. A port 33 with pneumatic seal 33a and a port 34 with pneumatic seal 34a lead to the internal passageway of the hollow cylindrical tube 10. A guide wire 35 is inserted through the pneumatic seal 33a and advanced into the hollow cylindrical tube 10 and through any arterial blockage. X-ray contrast dye is inserted by syringe through the pneumatic seal 34a.

An electrical on/off switch 36 and an open/close pneumatic switch 37 respectively control the application of the IR laser energy and vacuum to the hollow cylindrical tube 10. More particularly, the electrical switch 36 is electrically and physically connected by way of a conducting wire 38 to the on/off input of IR laser control box 30. The open/close pneumatic switch 37 in turn is pneumatically sealed to the inner walls of the hollow cylindrical tube 10, and is physically connected by way of a control wire 37a to a control lever 39. The control wire 37a moves up and down through a pneumatic seal in the wall of the hollow cylindrical tube 10. When the lever 39 is depressed, the electrical switch 36 applies an internal battery voltage by way of conducting wire 38 to activate the IR laser control box 30. Infrared radiation is thereupon applied through the optical fibers 13a and 13b to heat up a metal clad tip ring to the temperature specified by the control dial 30a. Simultaneously upon depressing lever 39, the open/close switch 37 is forced to open the interior passageway of the hollow cylindrical tube 10 to the vacuum applied by way of vacuum tube 40 to draw arterial debris out of the hollow cylindrical tube 10 and into a collection vessel 41. The vacuum tube 40 is pneumatically sealed at one end to the inner walls of hollow cylindrical tube 10, and is inserted through a pneumatic seal 41a into the collection vessel 41. The previously described vacuum tube 32 also is inserted through the vacuum seal 41a into the collection vessel 41.

When the lever 39 is raised, the electrical switch 36 ceases to apply a voltage to the conducting line 38. The IR laser control box 30 is thereby turned off. Simultaneously upon raising the lever 39, the open/close switch 37 is closed to prevent the vacuum applied by way of vacuum control box 31, pneumatic connector 31c, vacuum tube 32, collection vessel 41, and vacuum tube 40 from being applied to the interior of the hollow cylindrical tube 10.

In operation, the catherization system of the present invention comprising the hollow cylindrical tube 10 is inserted into an artery. X-ray contrast dye is inserted by syringe into the hollow cylindrical tube 10 by way of port 34 to pinpoint the location of any arterial blockage by means of X-Ray exposure. The guide wire 35 is inserted through the pneumatic seal 33a and advanced through the port 33 into the hollow cylindrical tube 10 past the arterial blockage. The catherization system embodiment comprising the hollow cylindrical tube 10, optical fibers 13a and 13b, and a metal clad tip ring as illustrated by any of the embodiments illustrated in FIGS. 1–4 is advanced along the guide wire 35 to abut the artery blockage. The control dials 30a and 31a thereafter are respectively set to the desired temperature and vacuum. The lever 39 then is depressed to activate the IR laser control box 30 and to open switch 37. In response thereto, the IR laser control box applies infrared radiation through the IR optic fibers 13a and 13b to heat the metal clad tip ring. Simultaneously, a vacuum is created within the inner walls of the hollow cylindrical tube 10. The IR optical fibers are raised to a temperature in excess of 172 degrees Fahrenheit to heat the metal clad tip ring and thermally cut or vaporize the arterial blockage. The vacuum is preferably in the range of 12 to 14 inches of mercury, and acts to draw into collection vessel 41 any arterial debris resulting from the above operation. More particularly, such debris is drawn out of the artery, through the longitudinal passageway created by the inner walls of the hollow cylindrical tube 10, and into the collection vessel 41 without allowing any debris to escape into the body blood stream.

Upon completion of the above operation, or as otherwise desired, the lever 39 may be raised to shut down the IR laser of the IR laser control box 30, and to close the open/close switch 37 to isolate the collection vessel from the forward portions of hollow cylindrical tube 10. The dial 31a then may be rotated counterclockwise to turn the vacuum off, and the collection vessel 41 may be disengaged from the pneumatic seal 41a to empty out any arterial debris which has been collected. The collection vessel 41 then may be cleaned and sterilized, and reengaged to the pneumatic seal 41a to conduct further arterial operations.

The present invention has been particularly shown and described in detail with reference to plural preferred embodiments, which are merely illustrative of the principles of the invention and are not to be taken as limitations to its scope. Further, it will be readily understood by those skilled in the art that numerous variations, changes, and modifications may be made without departing from the spirit of the invention. It is intended that the claims be interpreted to cover such variations, changes, and modifications.

What is claimed is:

1. An arterial catherization system for removing arterial blockage from an artery, which comprises:
    a cylindrical tube having a longitudinal passageway and at least one port;
    an annular tip axially aligned and abutting said cylindrical tube to effect a thermal cutting of said arterial blockage and to provide an entry into said longitudinal passageway for removing arterial debris;
    plural optical fibers pneumatically sealed within and extending along a longitudinal axis of said cylindrical tube, and abutting said annular tip to accommodate a heating of said annular tip to a thermal cutting temperature; and
    arterial guards formed into and extending from an outer surface of said cylindrical tube to separate inner walls of said artery from said annular tip and outer walls of said cylindrical tube, thus avoiding physical and thermal damage to said artery and providing blood pathways around said arterial catherization system to downstream body tissue.

2. The arterial catherization system of claim 1, wherein removal of said arterial debris occurs through a vacuum in said longitudinal passageway.

3. The arterial catherization system of claim 1, wherein said plural optical fibers are IR optical fibers.

4. The arterial catherization system of claim 1, wherein said annular tip is longitudinally separated from said cylindrical tube to provide alternative pathways for blood to enter said longitudinal passageway.

5. The arterial catherization system of claim 1, wherein said annular tip has a first circumference adjacent said cylindrical tube which is smaller than a second circumference of said annular tip which is further most from said cylindrical tube.

6. The arterial catherization system of claim 5, wherein said first circumference remains constant along said longitudinal axis a first distance and thereafter progressively increases to said second circumference, thereby providing an extended cutting surface to avoid clogging by said arterial debris.

7. A catherization system for removing blockage from an artery, which comprises:
    a tube having a central passageway for blood flow;
    plural optical fibers pneumatically sealed within inner and outer walls of said tube and extending a longitudinal length of said tube;
    an annular metal clad tip ring affixed to an end of said tube and abutting said plural optical fibers;
    plural arterial guards affixed to an outer surface of said tube and extending laterally to hold inner walls of said artery from said annular metal clad tip ring and said tube;
    a radiation source in optical communication with said plural optical fibers for applying heat to said metal clad tip ring to thermally cut through said blockage; and
    a vacuum system in pneumatic communication with said tube for creating a vacuum within said central passageway for accommodating a blood flow current to remove arterial debris dislodged by said annular metal clad tip ring from said artery.

8. The catherization system of claim 7, wherein edges of said plural arterial guards are rounded, and said tube includes an outer Teflon coating to avoid any physical and thermal damage to said artery.

9. The catherization system of claim 7, wherein said annular metal clad tip ring has a first circumference adjacent said tube which is smaller than a second circumference at a cutting edge of said annular metal clad tip.

10. The catherization system of claim 7, wherein said annular metal clad tip ring has a vertical annular surface abutting said end of said tube, and a second annular surface coaxial with said vertical annular surface and slanting outward from said vertical annular surface.

11. The catherization system of claim 7, wherein said plural arterial guards are positioned near said end of said tube.

12. The catherization system of claim 7, wherein said annular metal clad tip ring is affixed to ends of said plural optical fibers, and separated along a longitudinal axis of said hollow cylindrical tube from said end of said tube to form a blood flowpath into the interior of said hollow cylindrical tube.

13. The catherization system of claim 7, wherein said hollow cylindrical tube is plastic and said metal clad tip ring is gold.

14. The catherization system of claim 7, wherein said plastic is a flexible polyvinal chloride (DEHP) type of plastic.

15. The catherization system of claim 7, wherein said tube has an external Teflon coating to further protect said inner walls of said artery from thermal damage.

16. A catherization method for removing blockage from an artery without damaging interior artery walls, which comprises the following steps:
    inserting dye into said artery to pinpoint position to said blockage through X-Ray exposure;
    inserting a guide wire into said artery to extend through said blockage;
    advancing a catherization system having a central passageway and a thermal cutting tip along said guidewire to abut said blockage;
    thermally cutting through said blockage by irradiating said cutting tip without damaging arterial walls; and
    removing arterial debris resulting from the above step of thermally cutting by creating a vacuum in said central passageway to avoid downstream damage caused by said arterial debris being carried into a body blood stream,
    where physical and thermal damage to said arterial walls is prevented by molding plural arterial guards into an outer surface of said catherization system.

17. The catherization method of claim 16 above, wherein said dye is an X-Ray contrast dye.

18. The catherization method of claim 16 above, wherein the step of thermally cutting is accomplished by an IR laser irradiating through IR optical fibers to heat said cutting tip.

* * * * *